(12) United States Patent
Rausch

(10) Patent No.: US 7,514,598 B2
(45) Date of Patent: Apr. 7, 2009

(54) TRANSGENIC PLANTS AND PLANT CELLS WITH REDUCED EXPRESSION OF INVERTASE INHIBITORS

(76) Inventor: Thomas Rausch, Im Neuenheimer Feld 360, D-69120 Heidelberg (DE)

( * ) Notice: Subject to any disclaimer, the term of this patent is extended or adjusted under 35 U.S.C. 154(b) by 351 days.

(21) Appl. No.: 10/785,367

(22) Filed: Feb. 23, 2004

(65) Prior Publication Data

US 2004/0250312 A1 Dec. 9, 2004

Related U.S. Application Data

(63) Continuation-in-part of application No. 09/762,782, filed as application No. PCT/EP99/05890 on Aug. 11, 1999, now Pat. No. 6,784,339.

(30) Foreign Application Priority Data

Aug. 12, 1998 (DE) ............................... 198 36 405

(51) Int. Cl.
*A01H 5/00* (2006.01)
*A01H 5/10* (2006.01)
*C12N 15/29* (2006.01)
*C12N 15/82* (2006.01)

(52) U.S. Cl. ................. 800/284; 800/285; 800/286; 800/287; 800/298; 800/306; 800/312; 800/320; 800/320.1; 800/320.2; 800/320.3; 800/322

(58) Field of Classification Search ............... 800/278, 800/281, 284, 285, 286, 287, 298, 306, 320, 800/312, 320.1, 320.2, 320.3, 322, 323
See application file for complete search history.

(56) References Cited

U.S. PATENT DOCUMENTS 6,384,300 B1    5/2002    Rausch ................. 800/284
6,784,339 B1 *  8/2004    Rausch ................. 800/286

FOREIGN PATENT DOCUMENTS

EP    0 442 592      8/1991
WO    WO 97/07221    2/1997
WO    WO 98/04722    2/1998

OTHER PUBLICATIONS

Link M. et al., FEBS Letters; 2004, vol. 573 pp. 105-109.*
Rausch T. et al., Biochimica et Biophysica acta, 2004; vol. 1696, pp. 253-261.*
S. Greiner, et al., "Cloning of A Tobacco Apoplasmic Invertase Inhibitor", *Plant Physiology*, (1998) 116: 733-742.
S. Krausgrill, et al., "In Transformed Tobacco Cells The Apoplasmic Invertase Inhibitor Operates As A Regulatory Switch of Cell Wall Invertase", *The Plant Journal*, (1998) 13(2): 275-280.
S. Krausgrill, et al., "Regulation of Cell Wall Invertase by A Proteinaceous Inhibitor", *Journal of Experimental Botany*, Great Britain, Oxford University Press, vol. 47, pp. 1193-1198.
A. Sander, et al., "Sucrose Protects Cell Wall Invertase But Not Vacuolar Invertase Against Proteinaceous Inhibitors", *FEBS Letters*, NL, Elsevier Science Publishers, Amsterdam, vol. 385, No. 3, pp. 171-175.
S. Greiner, et al., "Ectopic Expression of A Tobacco Invertase Inhibitor Homolog Prevents Cold-Induced Sweetening of Potato Tubers", *Nature Biotechnology*, vol. 17, Jul. 1999, pp. 708-711.
H. Weber, et al., "Sugar Import and Metabolism During Seed Development", *Trends in Plant Science*, May 1997, vol. 2, No. 5, pp. 169-174.
P. Broun et al., Jul. 31, 2001, PNAS, vol. 98, No. 16, pp. 8925-8927.
P. Broun et al., Nov. 13, 1998, Science vol. 282, pp. 1315-1317.
P. Elomaa et al., Molecular Breeding 1996, 2: pp. 41-50.
D. Bussis et al., Planta 1997, 202: pp. 126-136.
Gordon-Kamm et al. The Plant Cell, Jul. 1990, vol. 2, pp. 603-618.

* cited by examiner

*Primary Examiner*—Russell Kallis
(74) *Attorney, Agent, or Firm*—Ostrolenk, Faber, Gerb & Soffen, LLP

(57) ABSTRACT

The invention relates to transgenic plants and plant cells comprising a reduced expression of invertase inhibitors. The modification of the expression of the invertase inhibitors is achieved by introducing a cDNA sequence in an antisense orientation with respect to a promoter. The expression of the antisense DNA sequence is under the regulation of either the CaMV35S promoter or a tissue specific promoter.

27 Claims, 7 Drawing Sheets

*Nt-Inh1*: apoplasmic invertase inhibitor: (accession number: Y12805)

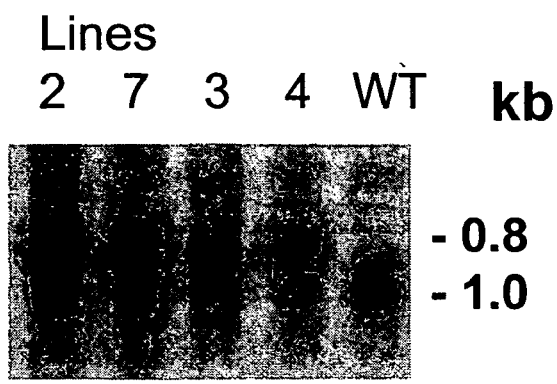

FIG. 7

```
  1 agaaaatcta actttggttc tctctctctt gtcttttcca acttcaaaaa tgaagaattt
 61 gattttccta acgatgtttc tgactatatt actacaaaca aacgccaata atctagtaga
121 aactacatgc aaaagcacac caaattacca actttgtctg aaaactctgc tttcggacaa
181 acgaagtgca acaggggata tcacaacgtt ggcactaatt atggtcgatg caataaaagc
241 taaagctaat caggctgcag tgacaatttc gaaactccgg cattcgaatc cccctgcagc
301 ttggaaaggt cctttgaaaa actgtgcctt ttcatataag gtaattttaa cagcaagttt
361 gcctgaagca attgaagcat tgacaaaaga agatccaaaa tttgctgaag atggaatggt
421 aggttcatct ggagatgcac aagaatgtga ggagtatttc aagggtagta atcaccatt
481 ttctgcatta aatatagcag ttcatgaact ttctgatgtt gggagagcta ttgtcagaaa
541 tttattgtga tatatatgca ctactcttat acaagtgtaa caatattatc gatcagaaat
601 ttattatgat gtgcctgtgt attcacacgt gaaaaaaaaa aaaaaaaaa
```

FIG. 8

SEQUENCE LISTING

```
<160> NUMBER OF SEQ ID NOS: 1

<210> SEQ ID NO 1
<211> LENGTH: 649
<212> TYPE: DNA
<213> ORGANISM: Nicotiana tabacum

<400> SEQUENCE: 1
agaaaatcta actttggttc tctctctctt gtcttttcca acttcaaaaa tgaagaattt      60
gattttccta acgatgtttc tcactatatt actacaaaca aacgccaata atctagtaga    120
aactacatgc aaaagcacac caaattacca actttgtctg aaaactctgc tttcggacaa    180
acgaagtgca cagggata tcacaacgtt ggcactaatt atggtcgatg caataaaagc      240
taaagctaat caggctgcag tgacaatttc gaaactccgg cattcgaatc ccctgcagc    300 ttggaaaggt cctttgaaaa actgtgcctt ttcatataag gtaattttaa cagcaagttt    360
gcctgaagca attgaagcat tgacaaaaga agatccaaaa tttgctgaag atggaatggt    420
aggttcatct ggagatgcac aagaatgtga ggagtatttc aagggtagta aatcaccatt    480
```

```
ttctgcatta aatatagcag ttcatgaact ttctgatgtt gggagagcta ttgtcagaaa        540
tttattgtga tatatatgca ctactcttat acaagtgtaa caatattatc gatcagaaat        600
ttattatgat gtgcctgtgt attcacacgt gaaaaaaaaa aaaaaaaaa                    649
```

TRANSGENIC PLANTS AND PLANT CELLS WITH REDUCED EXPRESSION OF INVERTASE INHIBITORS

RELATED APPLICATIONS

This is a continuation-in-part application of U.S. patent application Ser. No. 09/762,782, filed Mar. 30, 2001, now U.S. Pat. No. 6,784,339, which is based upon PCT International Application No. PCT/EP99/05890, filed Aug. 11, 1999, which in turn claims priority of German Application No. 198 36 405.9, filed Aug. 12, 1998.

BACKGROUND OF THE INVENTION

This invention concerns transgenic plant cells and plants, a method for their preparation and the use of invertase inhibitor cDNA sequences in an antisense or sense orientation to produce such plants.

Improvement in the quality and quantity of plant reserve material in seeds of dicotyledonous and monocotyledonous agriculturally-useful plants represents an important objective of biotechnology research. Hitherto, strategies generally were developed which were based on the introduction of particular genes whose genetic products constituted enzymes which are themselves involved in the synthesis of the energy reserves (e.g. ADP glucosepyrophosphorylase). Furthermore, methods are also described, in which an increased rate of glycolysis is obtained by modified expression of heterologous, and therefore, deregulated invertases or glucokinases in the cytosol (DE-A1-195 29 696). In later variants the increased breakdown of sucrose by a deregulated fungal invertase, in combination with a deregulated bacterial glucokinase, leads to an increased rate of glycolysis. This approach rests on the assumption that the synthesis of stored oils in seeds is stimulated because of the increased concentrations of the intermediates of glycolysis, since the metabolisation of the primary photoassimilate, sucrose, is required for phosphorylised hexoses or the fatty acid precursors, pyruvate and acetyl coenzyme A.

DE-A1-195 29 696 correspondingly describes the introduction of a foreign, e.g. fungal gene for the expression of the invertase. Because of the supply of the foreign gene, this fungal invertase enzyme (which is foreign and therefore is not subjected to any regulation) is formed in an amplified manner by regulating a suitable promoter, by means of which the decomposition of the sucrose catalysed by the invertase into glucose and fructose occurs faster. The resulting production of glucose at a higher rate is to bring about in the end an accelerated production of plant reserve material. This process is based on an intervention in the metabolism in the cell of the seed storage tissue, whereby the assimilate transfer between maternal and seed parenchyma is affected only indirectly.

The importance of cell wall invertase for the development of seeds high in starch and protein is well-known. Thus for example the starch accumulation in corn seed is adversely affected with reduced expression of a cell wall invertase by interference in the assimilate transfer between pedicel and endosperm. Flower-specific cell wall invertase isoforms for different plant species are well-known. For *Nicotiana tabacum*, it was able to be shown that an apoplastic invertase inhibitor is powerfully expressed, particularly in the ovary and stamens. Greiner et al. (Plant Physiol. (1998), 733-742) disclosed the amino acid sequence and cDNA sequence of the mentioned invertase inhibitor as well as its in vitro demonstration of function by means of a heterologous expressed inhibitor protein. However, in vivo inhibition was still not indicated. Moreover, it is well-known that varying isoforms of cell wall invertases and invertase inhibitors exist in different tissues and at different times in plant development.

A specific classification of the activities and their possible combined effects of these two time-specific and tissue-specific occurring proteins has not been feasible until now. There are no known studies of an in vivo situation with regard to the regulation of cell wall invertases by invertase inhibitors. Just as little known, was if and when which isoforms of the cell wall invertases are subjected to endogenous regulation by invertase inhibitors during the seed development and if so, which isoforms of the invertase inhibitors. That is why the specific use of these proteins for the production of beneficial plants has not been possible hitherto.

The technical problem of the invention therefore is to provide transgenic plant cells, plants and a method of producing these, in which the plants are characterised by the production of seeds which, compared to seeds of untransformed plants, have a greater amount of plant reserve material such as carbohydrates, fats or proteins, without endogenous or exogenous proteins being over-expressed and without the phenotype of the plant and its development being impaired.

SUMMARY OF THE INVENTION

The technical problem underlying this invention is provided by a process for producing a transgenic plant whose seeds have an increased amount of reserve material in comparison to a wild-type plant due to the reduction or elimination of the expression of an endogenous invertase inhibitor protein during the development of seeds, so that the activity of invertase, which is subject to a regulation by the invertase inhibitor protein, is increased during the development of seeds leading to an increased accumulation of reserve material in the seed, said process comprising the steps of:

a) obtaining a nucleotide sequence expressed during the seed development in flowers with young ovules;

b) inserting the nucleotide sequence in a DNA construct in sense or anti-sense orientation next to a promoter as a regulatory unit;

c) transforming a plant cell of a plant, from which the nucleotide sequence was obtained, with the DNA construct;

cultivating the plant cell and regenerating a plant, wherein the expression of the endogenous invertase inhibitor protein is reduced or eliminated during seed development.

BRIEF DESCRIPTION OF THE DRAWINGS

FIG. 7 shows a Northern Blot-Analysis of transformants with a BinAR-35S-Nt-inh1 sense construct.

FIG. 8 shows the sequence of the Nt-inh1-cDNA antisense strand with base substitution marked (SEQ ID NO:1).

DETAILED DESCRIPTION OF THE INVENTION

Figure 1:
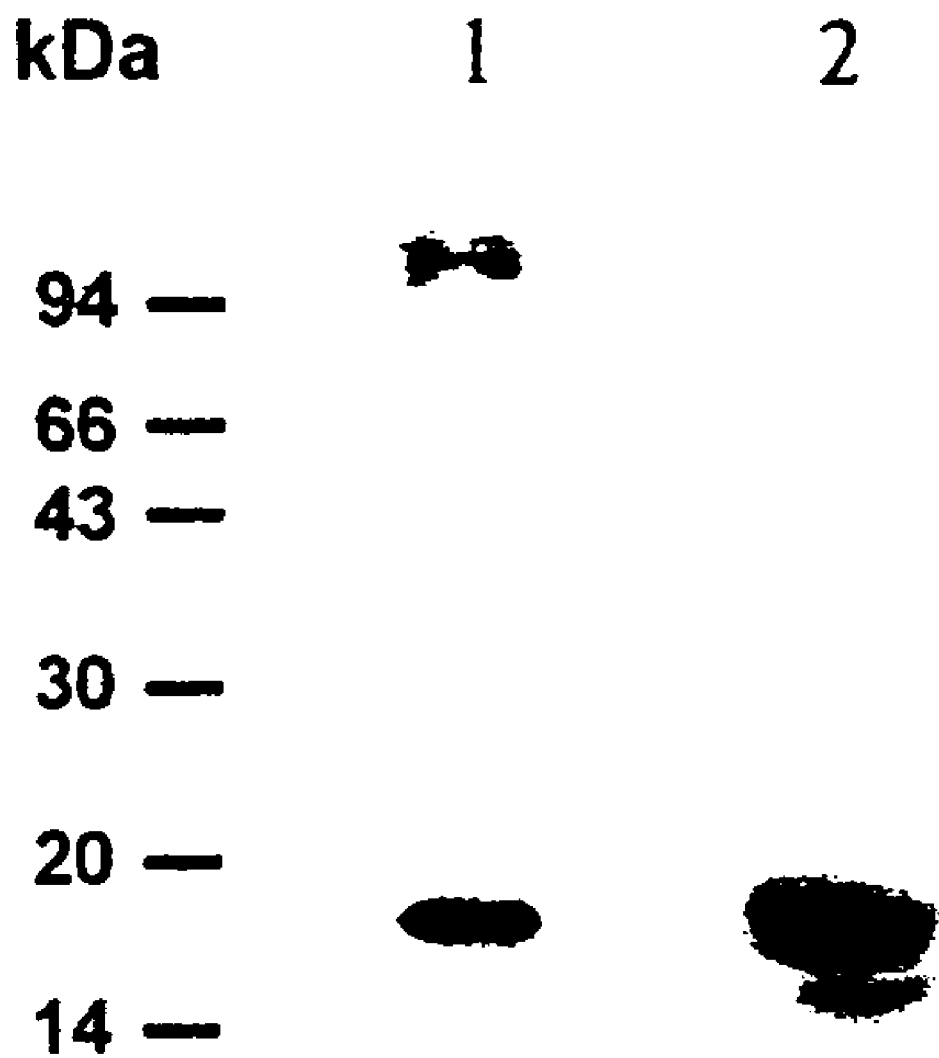
FIG. 1 shows the detection of invertase inhibitors in plants other than tobacco

According to the present invention, a DNA construct comprising a nucleotide sequence which is functionally linked with at least one regulatory unit such as a promoter is introduced into a plant cell from which a plant is regenerated afterwards. In the cellular and/or tissue environment of the plant, i.e. upon transformation, the DNA construct comprising the nucleotide sequence is able to eliminate or reduce the expression of an endogenous invertase inhibitor protein during the development of seeds. Since the invertase inhibitor protein regulates the activity of an invertase expressed during the development of seeds, the elimination or reduction of the expression of the endogenous invertase inhibitor protein leads to an increase of the activity of invertase during the development of seeds. This in turn leads to an increased accumulation of reserve material in the seed.

According to the invention, the nucleotide sequence contained in the DNA construct can be a sequence which codes for an invertase inhibitor protein which is expressed during the seed development in the seeds. In a preferred embodiment of the invention the nucleotide sequence used codes for that invertase inhibitor protein whose expression during seed development should be eliminated or reduced. In this embodiment therefore the nucleotide sequence is obtained, i.e. isolated from the same plant species in which afterwards the DNA construct comprising the nucleotide sequence is introduced in order to reduce or eliminate the expression of the endogenous invertase inhibitor protein during seed development. In another preferred embodiment, the nucleotide sequence codes for an invertase inhibitor protein expressed during seed development, however, it is obtained from another plant species. This means that the nucleotide sequence coding for the invertase inhibitor protein expressed during seed development is isolated from a first plant species and then introduced in form of a DNA construct in cells of a second plant species. That is, a nucleotide sequence coding for an invertase inhibitor protein and obtained from a first plant species is used to eliminate or reduce the expression of the endogenous invertase inhibitor protein during seed development in a second plant species. If the nucleotide sequence used for the inventive purposes is derived from another plant species, it preferably shows a great degree of homology to the nucleotide sequence coding for the endogenous invertase inhibitor protein, whose expression during seed development should be eliminated or reduced. That means, the nucleotide sequence obtained from the second plant species shows a great degree of homology to the corresponding nucleotide sequence, i.e. the sequence of the corresponding invertase inhibitor gene of the first plant species. In the context of the present invention the terms "homologous" or homology" denote the degree of identity existing between two nucleotide sequences. Under stringent hybridization conditions single-stranded homologous nucleotide sequences can anneal to each other and can form a heteroduplex, i.e. they can hybridise to each other. According to the invention the degree of homology between the nucleotide sequences from the first and second plant species is at least more than 70%, preferably more than 75%, more preferred more than 75%, most preferred more than 80%, in particular more than 85%, more than 90%, more than 95%, more than 96%, more than 97%, more than 98% and more than 99%.

The nucleotide sequence used according to the invention to eliminate or reduce the expression of the invertase inhibitor protein during seed development can also be a sequence, which encodes an invertase inhibitor protein, which is normally expressed in a tissue or organ of a plant other than seeds. For example, the nucleotide sequence used can code for an invertase inhibitor protein, which is normally expressed in the stem, leaves, roots etc. of a particular plant, but not in seeds. In that case the nucleotide sequence is inserted in the DNA construct under the functional control of appropriate regulatory units which guarantee or secure the expression of the gene product of the nucleotide sequence, i.e. of the invertase inhibitor in the seeds of the plants, in which the amount of reserve material should be increased. The person skilled in the art knows that for a plurality of plant species appropriate regulatory units such as promoters, which accomplish the expression of genes or gene products in seeds during the seed development exist. The nucleotide sequence used coding for an invertase inhibitor protein which is normally not expressed in seeds, can be isolated from that plant species, in which, according to the inventive process, the amount of reserve material is to be increased. According to the invention, however, the nucleotide sequence coding for an invertase inhibitor protein, which is normally not expressed in seeds, can also be isolated from another plant species, which is different from that plant species, in which, according to the inventive process, the amount of reserve material is to be increased. If the nucleotide sequence used for the inventive purposes is coding for an invertase inhibitor protein which is normally not expressed in seeds, it preferably shows a great degree of homology to the nucleotide sequence coding for the endogenous invertase inhibitor protein in seeds whose expression during seed development should be eliminated or reduced. According to the invention the degree of homology between the nucleotide sequence encoding the invertase inhibitor expressed in another tissue, i.e. not in seeds, and the nucleotide sequence, encoding the endogenous invertase inhibitor protein whose expression during the seed development should be eliminated or reduced, is at least more than 70%, preferably more than 75%, more preferred more than 75%, most preferred more than 80%, in particular more than 85%, more than 90%, more than 95%, more than 96%, more than 97%, more than 98% and more than 99%.

In another embodiment the nucleotide sequence used for the inventive process is a sequence which does not encode a functional invertase inhibitor, but which shares a great degree of homology with the nucleotide sequence encoding that endogenous invertase inhibitor, whose expression during seed development is to be eliminated or reduced. According to the invention, the degree of homology between the homologous nucleotide sequence, which does not code for a functional invertase inhibitor and the nucleotide sequence coding for the endogenous invertase inhibitor is at least more than 70%, preferably more than 75%, more preferred more than 75%, most preferred more than 80%, in particular more than 85%, more than 90%, more than 95%, more than 96%, more than 97%, more than 98% and more than 99%. In a preferred embodiment of the invention the homologous nucleotide sequence which does not encode an invertase inhibitor protein is derived form the nucleotide sequences coding an inhibitor protein, which is either expressed in the seeds, i.e. during seed development, or in another tissue or organ of the plant. Such homologous sequences, which do not encode an invertase inhibitor protein, can be obtained by the introduction of mutations in coding sequences, for example, by addition or deletion of one or more nucleotides, base substitutions, inversions, etc.

According to the invention the nucleotide sequences used in the inventive purposes can be shorter than the nucleotide sequence encoding the endogenous invertase inhibitor whose expression during seed development is to be eliminated or reduced.

The nucleotide sequences which show a high degree of homology to the nucleotide sequence of the endogenous invertase inhibitor protein whose expression in a plant, in particular in seeds of a plant, during seed development is to be reduced or eliminated, are characterized in that they contain at least a homologous stretch of nucleotides with a length of 20-25 base, i.e. this stretch is completely homologous to the corresponding stretch in the nucleotide sequence coding for the endogenous invertase inhibitor. That is, the homologous nucleotide sequences which can be used in the inventive process contain at least one region of 20 to 25 bp which shows a homology of 100% to the nucleotide sequence encoding the endogenous invertase inhibitor protein expressed during seed development. The nucleotide sequences used in the inventive process can either be isolated from natural sources, i.e. tissue or organs of a particular plant, or synthesized by chemical means.

The nucleotide sequences used in the inventive process can either be inserted in sense orientation or in anti-sense-orientation in the DNA construct. A DNA construct comprising one of the nucleotide sequences, which can be used in the inventive process, in sense-orientation induces in the seeds of the plant in which it was introduced, a co-suppression effect, which leads to an elimination or reduction of the expression of the endogenous invertase inhibitor gene during seed development. A DNA construct comprising one of the nucleotide sequences, which can be used in the inventive process, in anti-sense orientation induces in the seed of the plant in which it was introduced an anti-sense effect, which leads to an elimination or reduction of the expression of the endogenous invertase inhibitor gene during seed development. Both DNA constructs with the nucleotide sequence in sense orientation and DNA constructs with the nucleotide sequence in anti-sense orientation are targeted to the nucleotide sequence of the endogenous invertase inhibitor expressed in seeds and induce a post-transcriptional silencing of that nucleotide sequence in seeds.

In a preferred embodiment of the invention the inventive DNA construct induces upon introduction in the plant, in particular in the seeds of the plant, a RNAi (RNA interference) mechanism which leads to a post-transcriptional silencing of the endogenous invertase inhibitor gene during seed development, that is an elimination or reduction of the expression of that gene. Double-stranded RNA-mediated interference is a simple and rapid method of silencing gene expression in a range of organisms including plants. The silencing of a gene is a consequence of degradation of RNA into short RNAs that activate ribonucleases to target homologous mRNA. The first step involves degradation of dsRNA into small interfering RNAs (siRNAs), 21-25 nucleotides long, by an RNase III-like activity. In the second step siRNAs join an RNase complex which acts on the cognate mRNA and degrades it.

In order to induce an RNAi inhibition, preferably the DNA construct used for silencing the endogenous invertase inhibitor gene during seed development, encodes a double-stranded RNA and/or an inverted repeat RNA of the endogenous invertase inhibitor gene or a double-stranded RNA and/or an inverted repeat RNA of a nucleotide sequence which shows a high homology thereto. The construct preferably encodes a single-self complementary hairpin RNA of the nucleotide sequence used. The construct to be used contains two copies of the nucleotide sequence used for the inventive purposes, whereby one copy is in sense orientation and the second copy is in anti-sense orientation. The two copies preferably flank a spacer fragment which is non-homologous to the nucleotide sequence used and which has a length of about 100-1000 nucleotides. The spacer fragment only contributes to the stability of the perfect-repeat sequences, but is not required for the specificity of the post-transcriptional silencing. Therefore, the spacer can have any sequence except such sequences which are homologous to the sequence of the endogenous invertase inhibitor gene which is to be silenced. The spacer can comprise for example the sequence of an intron of another gene."

The technical problem underlying this invention is provided by a process for producing a transgenic plant with a deregulated invertase activity which stimulates plant development, whereby the process provides for: a nucleotide sequence of an invertase inhibitor to be produced from a cDNA bank of a cell suspension culture or from flowers with young ovules from a plant, or to be derived therefrom; a plant cell of a plant of the same type or variety with a DNA construct, containing the functional nucleotide sequence of an invertase inhibitor bound to at least one regulatory unit to be transformed, cultivated and regenerated to a plant whose seed produces a greater amount of reserve material such as carbohydrates, fat or protein in comparison with plants not transformed with such a DNA construct.

The invention provides in particular for the production of transgenic plants with a modified expression of an invertase inhibitor, preferably an apoplastic invertase inhibitor, whereby the plants are characterised by the expression of invertase inhibitor proteins being reduced or completely eliminated during seed development. The process can be applied advantageously to the most widely different dicotyledonous or monocotyledonous useful plants, for example: rape, sunflower, peanut, oil palm, soy bean, *Calendula officinalis*, *Coriandrum sativum*, *Crambe abyssinica*, *Cuphea* ssp., *Dimorphotheca pluvialis*, *Euphorbia lagascae*, *Euphorbia lathyris*, *Lesquerella grandiflora*, *Limnanthes alba*, *Linum usitatissimum*, *Lunaria annua*, *Lunaria biennis*, *Oenothera* ssp., *Ricinus communis*, and *Simmondsia chinensis* as plants with seeds storing fat; corn, rice, wheat, barley, oats, and rye as plants with seeds storing starch; and soy bean or pea, for instance, as plants with seeds storing protein.

Accordingly the invention provides for the transformation of a plant cell with a nucleotide sequence of an invertase inhibitor gene controlled by at least one regulatory unit, the nucleotide sequence of the invertase inhibitor gene being capable of eliminating or reducing the activity of a cell-specific endogenous invertase inhibitor. In a preferred form of implementation, elimination of the activity of an endogenous invertase inhibitor in the cell can be achieved, in that the nucleotide sequence of an invertase inhibitor is inserted in an antisense DNA construct, i.e. a construct in which a nucleotide sequence of the invertase inhibitor gene is in an antisense orientation with respect to a promoter. Through the expression, i.e. in this context the transcription of the antisense construct, the activity of the cell-specific invertase inhibitor gene is blocked or reduced so that the invertase deregulated in this way leads to an increased accumulation of reserve material in the seed.

In the context of this invention, an antisense construct is understood to mean a DNA construct which has a nucleotide sequence of an invertase inhibitor functionally bound in an antisense orientation to a promoter, this nucleotide sequence being either the full-length cDNA of the invertase inhibitor, a derived sequence thereof or a fragment, an allelic variant or derivative thereof.

In the context of this invention, a sequence derived from a cDNA is understood to mean a man-made or natural nucleotide sequence hybridising with this cDNA sequence, and therefore a nucleotide sequence hybridised with the cDNA sequence of the invertase inhibitor under the conditions described in Sambrook et al. (Molecular Cloning, a laboratory manual, $2^{nd}$ edition (1989), Cold Spring Harbor Laboratory Press), preferably under stringent conditions. According to the invention, hybridising sequences have a sequence identity of 60, 70, 80, 90, 95 or 97%, especially preferred 99%, of the cDNA sequence of an invertase inhibitor gene. Provided that fragments of a cDNA sequence of an invertase inhibitor are used according to the invention, the fragments have at least a length and sequence similarity, which is sufficient, due to hybridisation of a wild-type transcript, to inhibit the translation of an endogenously produced invertase inhibitor mRNA, for example a length of a few hundred base pairs. Obviously provision can also be made for the antisense constructs to have nucleotide sequences of an invertase inhibitor gene or to consist of those which are transcribed but not translated, i.e. untranslated regions, or so-called UTR's.

In the context of this invention, DNA constructs, which can cause the elimination or reduction of the activity of an endogenous invertase inhibitor gene, are understood to also mean DNA constructs which have a nucleotide sequence of an invertase inhibitor as defined above or a sequence derived therefrom, which are functionally bound in a sense orientation to at least one regulatory unit, e.g. a promoter. With constructs of this type, the production of endogenous invertase inhibitors can be prevented by co-suppression, for example by a plurality of sense copies of the nucleotide sequence of an invertase inhibitor being available in the genome of the transformed cell and eliminating the expression of endogenous invertase inhibitors.

The constructs according to the invention are preferably arranged in a vector, e.g. in a plasmid, virus, cosmid, bacteriophage or one other standard vector in gene technology.

Provision can be made according to the invention to not only functionally bind the nucleotide sequence of an invertase inhibitor, which is to be used, to a 5'-wards located promoter, but advantageously also to insert a transcription termination signal e.g. from the NOS gene of *Agrobacterium tumefaciens* 3'-wards of the nucleotide sequence. Obviously it also possible to provide additional functional units in the vector, such as T-DNA border sequences or elements stabilising the vectors.

The invention in a preferred way therefore provides plants which have in their seeds an increased amount of reserve material in comparison with untransformed plants, whereby an amount of reserve material increased in comparison means that the average amount of reserve material studied in seeds of a totality of transformed plants is greater than the average amount of the reserve material in question in the seeds of a totality of untransformed plants by predominantly 5, preferably 10, 20, 30, 40, 50, especially preferred 90, 100, 200 or 300%.

The invention therefore concerns the surprising science that, by means of a nucleotide sequence of an invertase inhibitor gene, in particular a cDNA of an invertase inhibitor gene, plants can be produced which in vivo have an increased accumulation of reserve material in the seed, without modifying or impairing the development of the plant in other respects. As well, the invention is based inter alia on the surprising fact that the endogenous invertases are subject to an endogenous regulation by invertase inhibitors during the seed development.

The invention therefore also concerns the use of a nucleotide sequence of an invertase inhibitor gene functionally bound to at least one regulatory unit for the transformation and production of plants which have a modified seed development, and in particular which produce seeds which have an increased amount of reserve material compared to seeds of untransformed plants.

The invention particularly concerns the afore-mentioned use of a nucleotide sequence of an invertase inhibitor gene, this having been obtained from a cDNA bank of a cell suspension culture or from flowers with young ovules of the plant type or if necessary of the plant variety, or having been derived therefrom, which is to be transformed according to the invention with the DNA construct of this invention produced by means of this nucleotide sequence. The nucleotide sequence used for the transformation is consequently the nucleotide sequence or is derived therefrom, which encodes for the predominant isoform of the invertase inhibitor in the cell suspension culture or in the flowers with young ovules.

In the context of this invention, flowers with young ovules are flowers with immature ovules, that is after pollination but before the start of dormancy.

The solution to the technical problem according to the invention is also a transgenic plant cell in which, in comparison with untransformed plant cells, an increased activity of the cell wall invertase is present because of reduced expression of invertase inhibitors, in which transgenic plant cell this reduced expression is produced in an antisense orientation by introducing an invertase inhibitor cDNA corresponding (homologous) to the same plant type and by regulating a promoter. According to the invention, a process for obtaining invertase inhibitor cDNA sequences in a sense orientation or antisense orientation is also provided, the process containing—independently of the respective species—the following steps:

a) producing an inhibitor protein fraction from the cell wall protein fraction of an appropriate cell suspension culture b) production of corresponding peptide sequences after separation and purification of the peptide formed c) cloning firstly partial cDNA and subsequently full-length cDNA for the invertase inhibitor protein from a cDNA bank d) cloning of the invertase inhibitor cDNA in a sense orientation or antisense orientation in a vector, e.g. a binary vector e) transformation of the plant species with the sense orientation or antisense construct.

The assimilate transfer between maternal tissue and seed tissue is the rate-determining step in the production of plant reserve material in seeds. If this step is accelerated by increasing the activity of the cell wall invertase expressed in the transfer zone, the result is an increased accumulation of the principal reserve material of the respective plant type (starch, fat, protein) as a result of the increased assimilate transfer (the increased activity of the cell wall invertase causes an increase in the assimilate transfer between maternal and seed tissue).

The invention also concerns a process for producing the afore-mentioned plants, whereby in a first step an inhibitor protein fraction, in particular the predominant inhibitor protein fraction, from a cell wall protein fraction is obtained from a cell suspension culture or from flowers with young ovules; then in a second step the inhibitor protein fraction is purified, if necessary separated, and at least N-terminal is sequenced, so that a nucleotide can be derived from the amino acid sequence thus obtained; within the framework of a third step by means of for example primers, partial or full-length cDNA for the invertase inhibitor protein is cloned from a cDNA bank of a cell suspension culture or from flowers with young ovules of the same plant or variety mentioned above, then in a fourth step the cDNA obtained is cloned in a vector in a sense orientation or antisense orientation, in order to subsequently transform in a fifth step a plant cell of the same type or variety with the DNA construct thus obtained, this being the type or variety from which the cDNA and the amino acid sequence for the cDNA isolation was obtained. From that, the invention also concerns plants, and plant components such as root, stem, leaves, cropping and propagating material such as fruit, pollen, seeds, husk, embryo, seedlings, cell cultures, callus tissues etc., produced in accordance with this process. The invention concerns as well any variety or type of plant, and accordingly has no specificity with regard to variety or type whatsoever. The process according to the invention represents an essentially technical process, whereby within its framework a specific allocation of starting material for the means to be used, such as cDNA sequences, is given to a plant, i.e. the target, which is to be transformed.

Unlike all previous methods, the invention described here is based therefore on the regulation of specific cell wall invertase isoforms expressed during the seed development. The invertase inhibitor cDNA in a preferred form of implementation encodes for an apoplastic variant of the invertase inhibitor. By introducing a single autologous cDNA sequence of plant origin, i.e. a cDNA sequence stemming from the organism to be transformed or derived therefrom, the decisive step in the separation of sucrose for the assimilate transfer is modulated at the natural location of activity. The observation that the introduction of at least one sequence, that is of one invertase inhibitor cDNA, in a sense orientation or antisense orientation by controlling, for example, the constitutive CaMV35S promoter, the ubiquitin promoter or zein promoter from corn or a promoter of similarly high or greater activity, e.g. a tissue-specific promoter as well which does not affect entire vegetative plant development, but results in a specific deregulation only during the seed development, shows the extremely high specificity of the transgenic intervention. The advantages of this direct deregulation are obvious: 1) one single gene construct is sufficient to achieve a significant modification of reserve material accumulation; 2) no foreign gene products are produced; 3) the intervention in the metabolism is extremely specific; 4) for tobacco, it is shown by example that the modified expression of an apoplastic invertase inhibitor leads to drastic changes in the production of stored oil.

The modulation, particularly the increase in the accumulation of the seed reserve materials, by a specific modification of the expression of the invertase inhibitor, especially reduction, is based inter alia on the following mechanisms:

a) by modifying the activity phase of the cell wall invertase in the maternal tissue, the efficiency of the nutrient load is affected, i.e. is increased for example in inhibitor antisense transforms.

b) The oxidative pentose phosphate cycle is of crucial significance for the synthesis of reserve oils of the seeds. The sustained increased availability of glucose in, for example, inhibitor antisense transforms therefore promotes the synthesis of stored oil.

c) by modifying the ratio of hexoses to sucrose, the cell division phase of the seed development is affected. By extending the activity phase of the cell wall invertase in, for example, inhibitor antisense transforms, the cell count per seed, for instance, is increased.

In comparison with the equally possible overexpression of the cell wall invertase(s) involved in the assimilate transfer, the approach of turning off the invertase inhibitors described here indirectly has even further advantages. The cell wall invertases expressed during seed production are heavily expressed naturally, the scope of additional induction by using strong promoters is limited by this, whereas a large increase in the activity of the cell wall invertase(s) can be obtained by the antisense switching off according to the invention of the inhibitor. In fact, by expressing a heterologous, deregulated, inhibitor-sensitive invertase with a signal peptide for the target control in the cell wall space, a similar effect could be achieved, but in this case foreign proteins have to be used. In addition, with a combination of the seed-specific promoters with a deregulated invertase used for this approach, there is a high risk that too great an expression results in undesired side effects. In contrast to this, in the process described here, the maximum activity of the naturally-occurring cell wall invertases is never exceeded, merely the time span of its activity is prolonged during the accumulation of reserve material. For these reasons, in each case of introducing a heterologous invertase, indirect regulation of the cell wall invertases is to be preferred over antisense expression of invertase inhibitors or, in the framework of the co-suppression technology, over sense DNA constructs and represents a significant technical improvement.

Methods for Obtaining a Homogenous Inhibitor Protein Fraction from the Apoplastic Cell Wall Protein Fraction of a Cell Suspension Culture A cell suspension culture is started from the respective plant species. The process for obtaining a cell culture follows standard protocols of plant tissue culture. As a rule, the cells are started as a shaking culture under sterile conditions in a complex nutrient medium with the addition of sucrose (carbon source). Under these cultivation conditions, plant cells express a cell wall invertase which is regulated by a likewise expressed invertase inhibitor.

The accumulation and purification of the invertase inhibitor is based on its binding to the cell wall invertase. First a cell wall protein fraction is extracted through incubation in 1M NaCl, 1 mM PMSF at 4° C. while shaking. Usually no cytosolic proteins are extracted doing this. The cell wall protein fraction obtained in this way is concentrated through ammonium sulfate precipitation (80%) or through membrane filtration. By means of subsequent chromatography in a concanavalin A column, a glycoprotein fraction is obtained which contains the glycosylated cell wall invertase and the invertase inhibitor bound to this. SDS-PAGE/Western blot analyses of the cell wall invertase fractions, and therefore invertase inhibitor-enriched fractions, obtained in this way with a polyclonal antiserum against the invertase inhibitor from tobacco cells, indicate the presence of invertase inhibitors, generally proteins of 15-25 kDa.

FIG. 1 shows the detection of invertase inhibitors of other plant types which are homologous to the tobacco invertase inhibitor-a Western blot analysis of cell wall protein samples obtained from suspension cultures of *Chenopodium rubrum* (1) and *Daucus carota* (2). The development was carried out with an antiserum produced against the recombinant tobacco invertase inhibitor. Invertase inhibitor polypeptides of approx. 17 kDa were detected for both species.

Further purification of the complexes consisting of cell wall invertase and invertase inhibitor is carried out through ion-exchange chromatography in a cation-exchanger, e.g. sulfopropylsephadex. After sequential chromatography, first of all via a pH gradient (pH8-12), after that via an NaCl gradient, a highly enriched preparation of the cell wall invertase is obtained in which the invertase inhibitor is present with the latter in the stable complex. The peak fractions of the final ion exchange purification are detected through SDS-PAGE/ Western blot analysis because of cell wall invertase e.g. with an antiserum against the carrot cell wall invertases. Moreover, the invertase activities of all fractions were determined in the coupled enzymatic test with hexokinase/glucose-6-phosphate dehydrogenase. The fractions with the strong cell wall invertase immune signal but low invertase activity contain the generally high-purity inhibitor protein.

Methods for Obtaining Peptide Sequences of the Purified Invertase Inhibitors

After the purification protocol described above, the inhibitor protein is sufficiently pure to become N-terminal unsequenced after electroblotting directly onto a PMDF membrane. After obtaining 100-500 µg of inhibitor protein, this can if necessary be purified again via SDS-PAGE and then can be digested by trypsin directly in the gel. The separation of the resulting peptides through reverse phase HLPC and its subsequent sequencing through Edman degradation is in accordance with standard procedures. The combination of N-terminal unsequencing and the sequencing of the peptides preserved during tryptic digestion results in sufficient sequencing information for cloning based on the RT-PCR process.

Process for Cloning, Firstly, Partial cDNA and Subsequently Full-Length cDNA for the Respective Invertase Inhibitor Protein from a cDNA Bank Starting from the preserved peptide sequence information, primer sequences are derived according to the genetic code. Standard algorithms are used for the optimum primer design. In another implementation, primers are designed with highly conservative sequence regions of the already known invertase inhibitor sequences from *Nicotiana tabacum, Lycopersicon esculentum, Arabidopsis thaliana* and *Citrus inshui*.

First a single strand cDNA synthesis is carried out according to standard procedures. For this, complete RNA is extracted in accordance with standard procedures from a cell suspension culture, or, in another implementation, from flowers with young ovules. A partial invertase inhibitor cDNA is then first amplified through RT-PCR. In one implementation, the amplification is cloned into the Bluescript vector. After sequencing and confirming a sequence homologous to the known invertase inhibitors, this partial cDNA is used as a probe for the production of full-length clones. For this, either a cDNA bank from a cell suspension culture, or in another implementation, a cDNA bank from flowers with young ovules, is started in accordance with standard procedures.

Cloning of the Invertase Inhibitor cDNA in a Sense Orientation or an Antisense Orientation in a Vector, for Example a Binary Vector In one form of implementation the invertase inhibitor cDNA cloned for each plant type is cloned in the binary vector BinAR (Bin19 derivative) (Höfgen and Willmitzer, Plant Sci. 66 (1990), 221-230). In one form of implementation, the CaMV35S promoter is used for both for antisense and sense constructs, but if necessary other promoters, for example tissue-specific promoters, also can be used.

Figure 2:
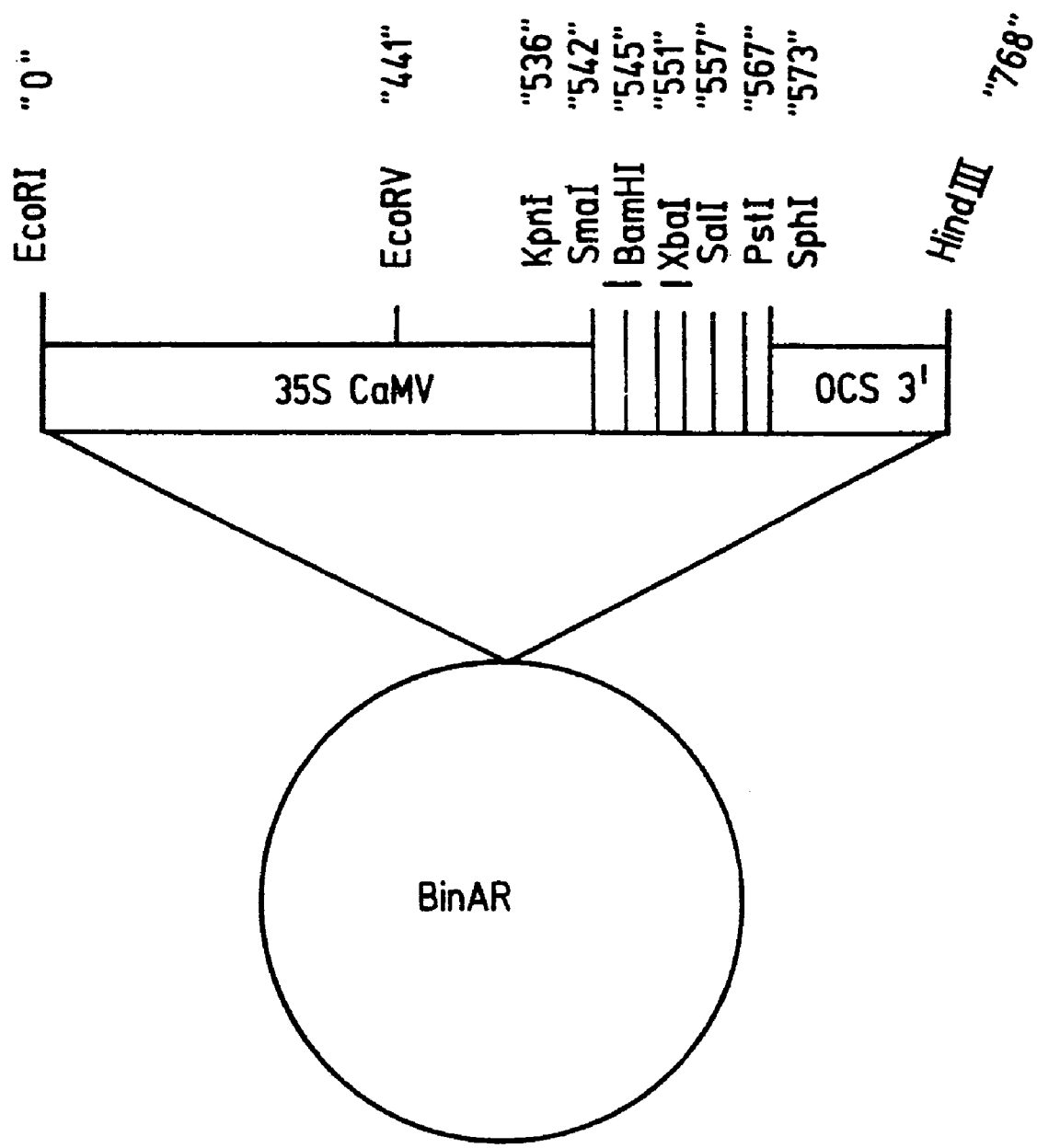
FIG. 2 shows the binary vector (BinAR) for *Agrobacterium tumefaciens*-mediated transformation.

FIG. 2 shows the binary vector (BinAR) for the *Agrobacterium tumefaciens*-mediated transformation. The encoding regions of the invertase inhibitor cDNA are cloned in a sense orientation or antisense orientation in the "multiple cloning site."

Transformation of the Plant Species with the Sense and Antisense Gene Constructs Respectively For most dicotyledonous useful plants, invertase inhibitor sense/antisense transforms are obtained by using *Agrobacterium tumefaciens*-mediated transformation (standard process). Accordingly an *Agrobacterium* is used, since it contains recombined DNA molecules which have invertase inhibitor cDNA in antisense orientation or sense orientation, i.e. in which the invertase inhibitor cDNA exists 3'-wards from a promoter and functionally bound with the latter. In a form of implementation useable for many plant types, leaf fragments are transformed with this, primary transforms being regenerated from the recombinant cells in an antibiotic-containing medium. The transformation technique actually selected is dependent on the plant type. A transgenic plant is obtained by regeneration of a transformed plant cell.

The influence of the modified expression of an apoplastic invertase inhibitor in *Nicotiana tabacum* is described below:

Tobacco (*Nicotiana tabacum*) was transformed in sense orientation and antisense orientation with the cDNA of the apoplastic tobacco invertase inhibitor (clone Nt-inh1; Greiner et al., *loc cit.* 1998) (*Agrobacterium tumefaciens*-mediated transformation, BinAR vector, CaMV35S promoter; leaf slice transformation according to standard procedures). The cDNA used was obtained from a cell suspension culture of tobacco. Primary transforms were first regenerated to plants via tissue culture and subsequently brought to flower in the greenhouse. The seeds of the primary transforms were sown on a kanamycin-containing medium. After sterile pre-cultivation the plants of the F1 generation were brought to flower in the greenhouse. After pollination the cell wall invertase activities in the ovaries were determined at regular time intervals.

Figure 3:
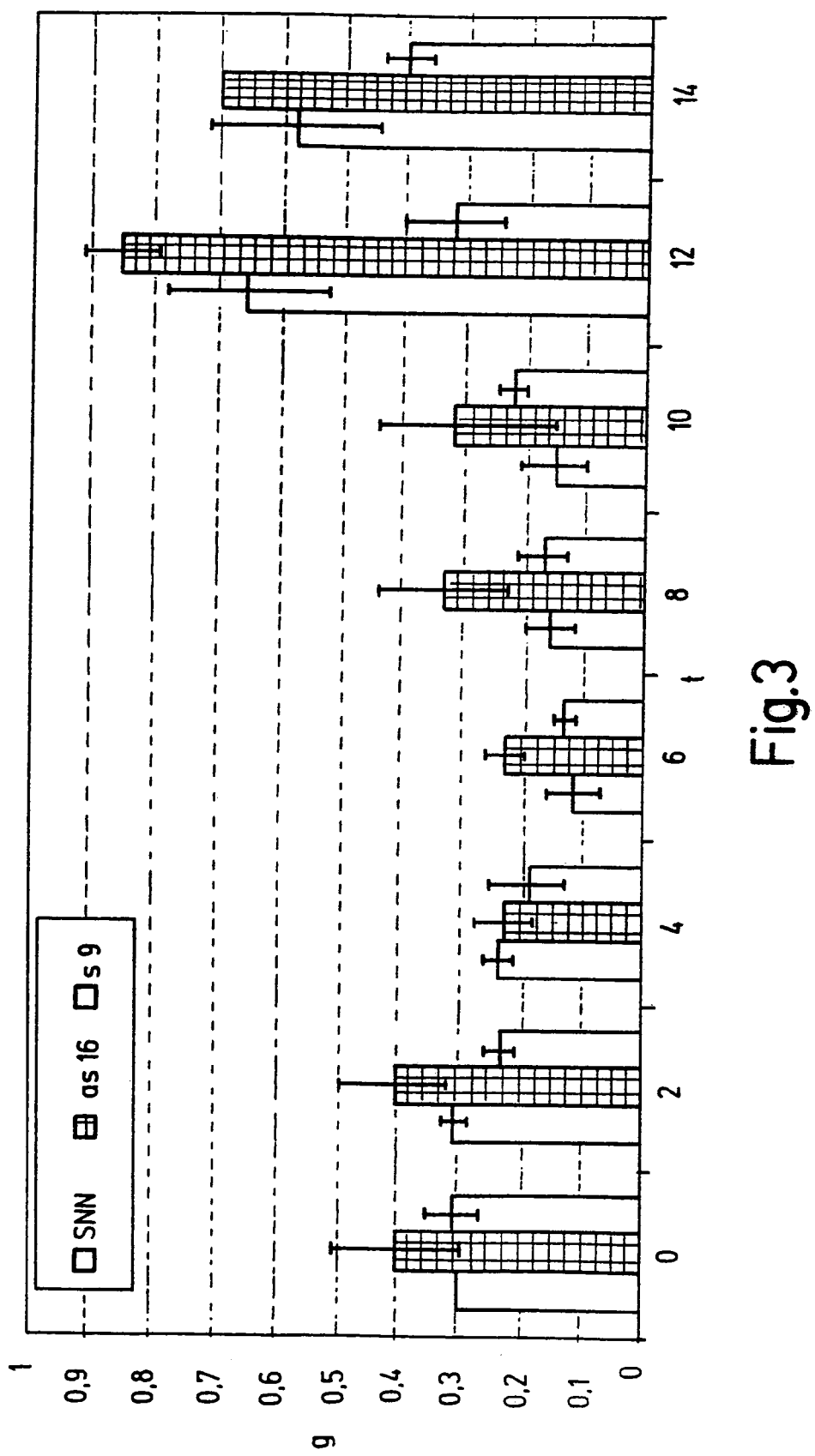
FIG. 3 shows cell wall invertase activities in the ovary of a tobacco wild-type (SNN), an antisense transformant (as16), and a sense transformant (s9).

FIG. 3 shows cell wall invertase activities in the ovary of a tobacco wild-type (SNN), a representative inhibitor antisense transform (as 16) and a representative inhibitor sense transform (s9) during the early seed development (0-14 days after fertilisation). The activities are indicated in mmol glucose/g fresh weight/min.

The amount of invertase inhibitor protein was determined through Western blot analysis.

Figure 4:
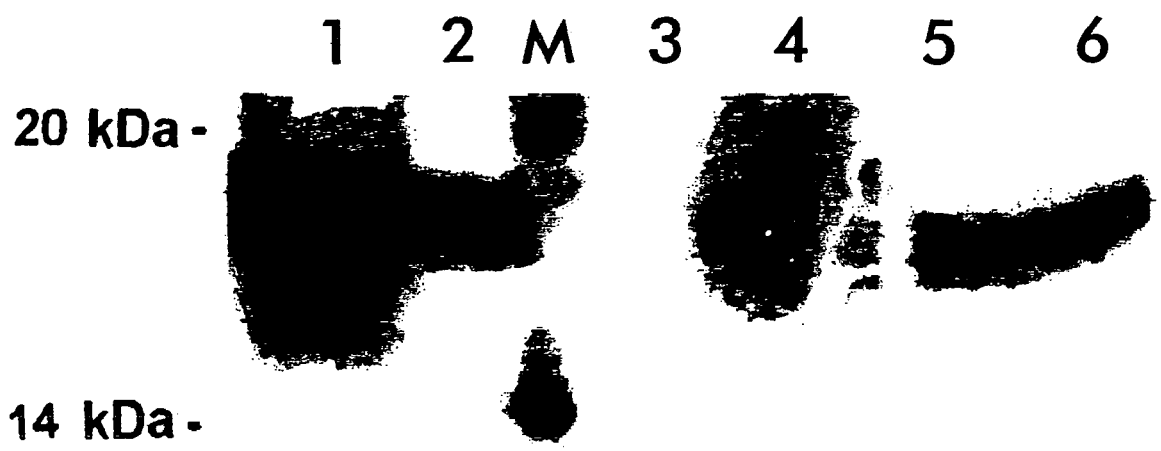
FIG. 4 shows the selective reduction or increase of the invertase inhibitor in stamens and ovaries.

With regard to this, FIG. 4 shows the proof of the selective reduction (antisense transform) or increase (sense transform) of the invertase inhibitor polypeptide in stamens and ovaries, detected with an antiserum directed against the recombinant tobacco invertase inhibitor (sense transform (s9): 1, ovaries; 2, stamens. Antisense transform: 3, ovaries; 4, stamens. Wild-type (SNN): 5, ovaries; 6, stamens). Purified samples, which contain an inhibitor bound only to a cell wall invertase, were plotted through concanavalin A chromatography.

After maturation of the seeds, their dry weights were determined, as well as the amount of stored oil and total protein.

Measurement of the cell wall invertase activities during the early seed development (FIG. 3) shows first of all an approximately 6-fold increase for the wild-type between the $6^{th}$ and $12^{th}$ day after pollination. This period corresponds to the late cell division phase and the beginning of the storage phase. The Western blot analysis shows that in the ovary the amount of invertase inhibitor polypeptide in antisense transforms is sharply decreased, however it is greatly increased in antisense transforms (FIG. 4). In contrast to this, the modified inhibitor expression is obtained only slightly in stamens, presumably because several inhibitor isoforms are expressed in this tissue.

The modified activity of the cell wall invertase during the seed development has an effect on the dry weight/seed (Table 1), the stored oil content/seed (Table 2) and the total protein content/seed (Table 3), but not on the total number of seeds per flower and also not on the seed size.

TABLE 1

Dry weight per seed in tobacco wild-type (SNN), in two representative inhibitor sense transforms (s9, s10) and in two representative inhibitor antisense transforms (as16, as43).

| Tobacco Line | µg Dry Weight/Seed | Percent of Wild-type (SNN) |
| --- | --- | --- |
| WT (SNN) | 64 ± 2 | 100 |
| s9 | 42 ± 2 | 66 |
| s10 | 52 ± 2 | 81 |
| as16 | 71 ± 1 | 110 |
| as43 | 86 ± 4 | 134 |

TABLE 2

Seed oil content per seed in tobacco wild-type (SNN), in two representative inhibitor sense transforms (s9, s10) and in two representative inhibitor antisense transforms (as16, as43).

| Tobacco Line | µg Total Oil/Seed | Percent of Wild-type (SNN) |
| --- | --- | --- |
| WT (SNN) | 23 | 100 |
| s9 | 10 | 43 |
| s10 | 16 | 69 |
| as16 | 28 | 122 |
| as43 | 39 | 170 |

TABLE 3

Total protein per seed in tobacco wild-type (SNN), in two representative inhibitor sense transforms (s9, s10) and in two representative inhibitor antisense transforms (as16, as43).

| Tobacco Line | µg Total Protein/Seed | Percent of Wild-type (SNN) |
| --- | --- | --- |
| WT (SNN) | 7.4 | 100 |
| s9 | 5.5 | 74 |
| s10 | 5.7 | 77 |
| as16 | 7.8 | 105 |
| as43 | 9.9 | 134 |

The large increase in stored oil content in two individual antisense transforms (+22% and +70% respectively) correlates with increases in total protein and seed weight, the increase for stored oil being most marked. Remarkably the increase in the cell wall invertase activity in the ovary during the seed development corresponds to the phase of the maximum accumulation of stored oil.

The entire vegetative development phase of the inhibitor antisense and inhibitor sense transforms proceeds with no visible phenotype, with the exception of the germination process. Here there is no difference between the germination of tobacco wild-type seeds and invertase inhibitor antisense seeds, whereas with seeds of invertase inhibitor sense transforms there is a significant delay in germination.

Figure 5:
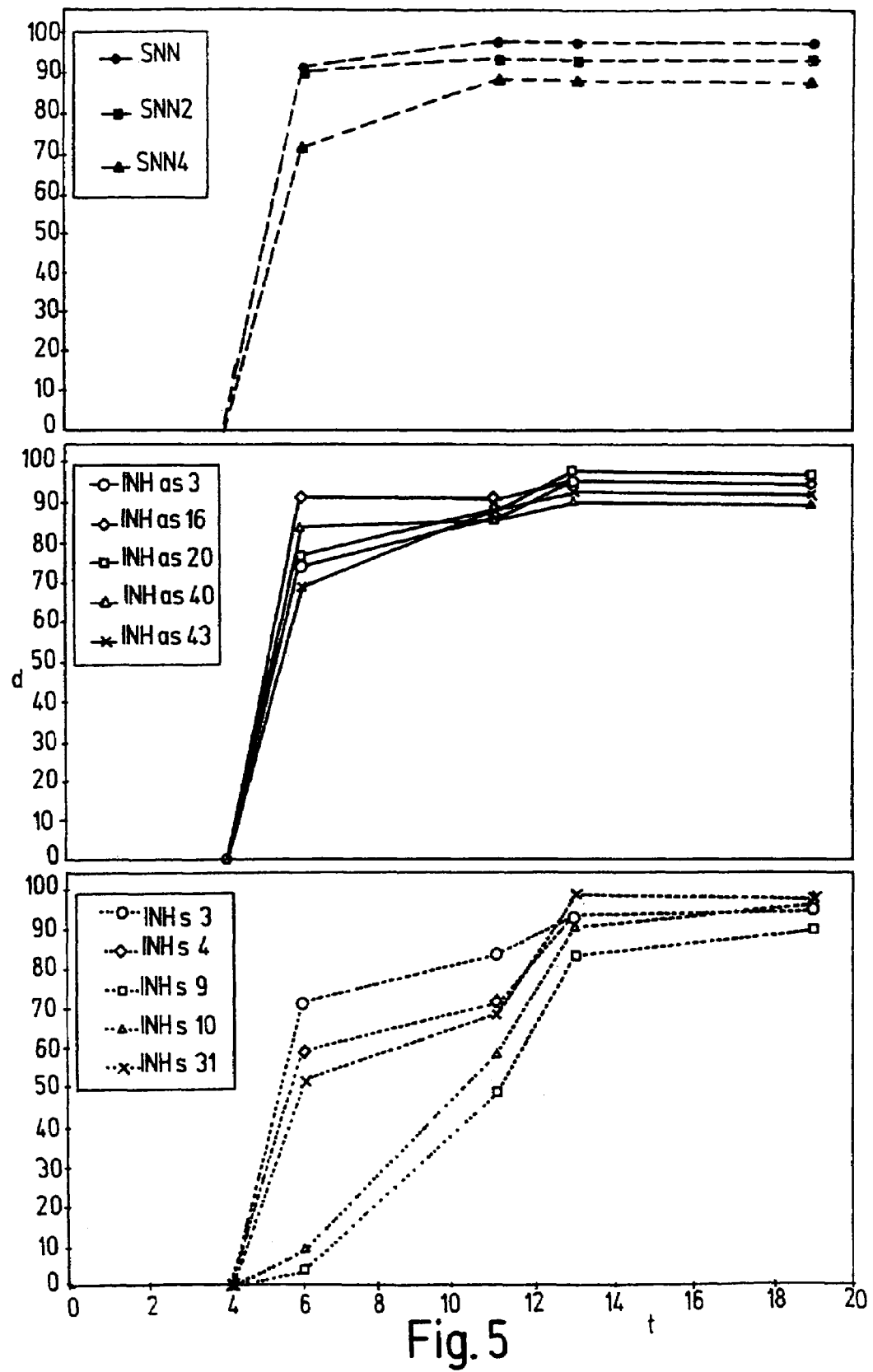
FIG. 5 shows germination of wild-type, antisense transformant, or sense transformant tobacco seeds.

FIG. 5 shows the germination behaviour of seeds of tobacco wild-type (SNN), of invertase inhibitor antisense transforms (INHas) and of invertase inhibitor sense transforms. Per line, in each case 40 seeds were sown on an LS medium (0.5% sucrose, pH5.6) under sterile conditions. The protrusion of the radicle is used as the criterion for germination.

A further example of application of this invention is the introduction of an invertase inhibitor antisense construct in rape (*Brassica napus*). On a seed basis, rape contains an amount of stored oil comparable to tobacco. The result of an invertase inhibitor antisense transformation is an increase in the stored oil content by at least 20%, and possibly by up to 70%.

A further application with the same objective, namely increasing the stored oil content, is the transformation of the sunflower, or perhaps the transformation of the soy bean, with an invertase inhibitor antisense construct (making available transgenic oil-storing plants of these species).

In an additional form of implementation, the amount of seed stored starch is increased by putting invertase inhibitor antisense constructs into corn, rice, wheat, oats, barley and rye. Thus transgenic plant cells or plants, which store starch, can be provided. In a further form of implementation, for protein-rich seeds, e.g. soy bean and pea, the total amount of stored protein is increased by introducing invertase inhibitor antisense constructs.

In an additional implementation form, the germinating capability of seeds of a useful plant is increased by introducing invertase inhibitor antisense constructs, or that is to say, by the enhanced reserve material accumulation resulting therefrom.

The preparation of transgenic plant cells or plants preferably concerns useful plants. In addition to the reduction of the amount of Nt-inh1 transcripts observed in transformants obtained upon transformation of *Nicotiana tabacum* with a construct comprising Nt-inh1 in anti-sense orientation, further experiments showed that also the use of constructs comprising Nt-inh1 in sense-orientation result in transformants with a reduced amount of Nt-inh1 mRNA in the seeds. Therefore, these transformants show a co-suppression effect. The influence of the reduced Nt-inh1 expression in seeds of transgenic plants obtained by use of sense constructs on the seed filling, i.e. the increased amount of reserve material in seeds of transgenic plants, was similar to that observed in transformants containing corresponding anti-sense constructs. In tobacco transformants, obtained by the use of constructs comprising Nt-inh1 in sense-orientation, both the dry weight/seed, the stored oil content/seed and the total protein content/seed were increased in comparison to seeds of wild-type tobacco plants.

These results show that also Nt-inh1 sense constructs can be used in order to produce transgenic plants whose seeds have an increased amount of reserve material in comparison to wild-type plants. This increased amount of reserve material is due to the reduction or elimination of the expression of the endogenous invertase inhibitor protein during the development of seeds by co-suppression, which in turn leads to an increased activity of the invertase which is normally regulated by the invertase inhibitor.

Further experiments show that not only the nucleotide sequence encoding the endogenous invertase inhibitor protein expressed during seed development can be used in order to increase the amount of reserve material in transgenic plants, but also nucleotide sequences, which are not completely identical thereto. That means, also nucleotide sequences can be used for the inventive purposes which have a high degree of homology to the nucleotide sequence of the endogenous invertase inhibitor, whereby, however, these nucleotide sequences show some differences such as base substitutions in comparison to the sequence of the endogenous invertase inhibitor gene. The experiments revealed that such homologous nucleotide sequence must contain a sufficiently long homologous region in order to eliminate or reduce the expression of the endogenous invertase inhibitor gene, whereby the length of this region should be at least 20 to 25 bp. In the experiments conducted, DNA constructs were created which either comprise one copy of such a non-identical homologous nucleotide sequence in sense-orientation or in anti-sense-orientation or two copies of such a non-identical homologous nucleotide sequence both in anti-sense and sense-orientation. After transformation of tobacco cells with these constructs transgenic tobacco plants were obtained whose seeds showed an increased dry weight/seed, an increased stored oil content/seed and an increased total protein content/seed in comparison to seeds of wild-type tobacco plants.

The experimental data obtained shows that the inventive process can be affected by the use of homologous nucleotide sequences which are in comparison to the nucleotide sequence of the endogenous invertase inhibitor, whose expression during seed development is to be eliminated or reduced, mutated. Furthermore, the experimental data shows that even homologous nucleotide sequences which do not encode a functional invertase inhibitor protein can be used in transgenic plants in order to eliminate or reduce the expression of the endogenous invertase inhibitor protein during the development of seeds and consequently to increase the amount of reserve material in the seeds.

Figure 6:
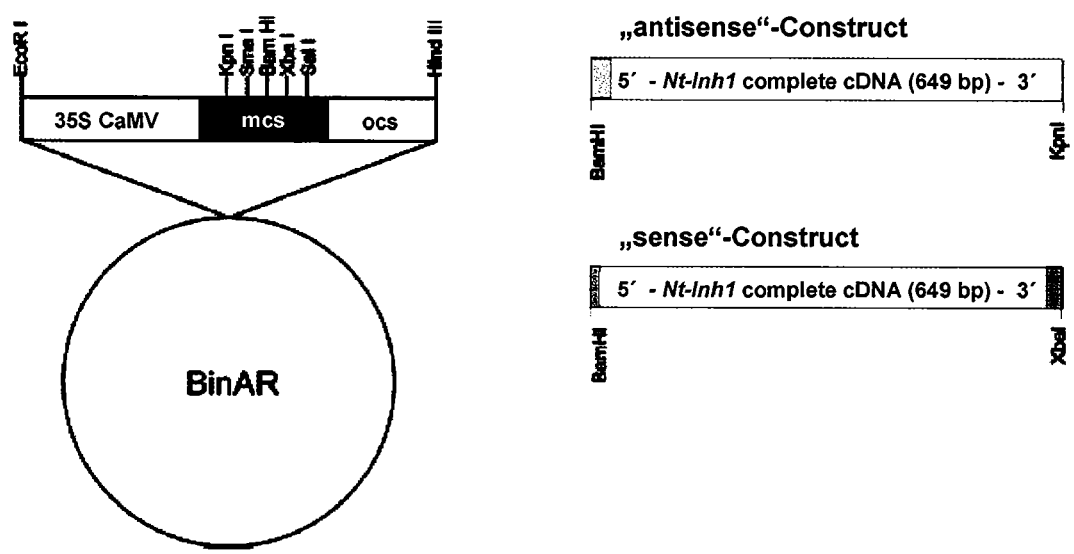
FIG. 6 shows the cloning strategy for the generation of BinAR-35S-Nt-inh1-sense and BinAR-35S-Nt-inh1-antisense constructs for the transformation of tobacco.

BinAR-35S-Nt-inh1-sense and BinAR-35S-Nt-inh1-antisense constructs for the transformation of tobacco were cloned as described FIG. 6. Northern Blot-Analysis was conducted on transformants with a BinAR-35S-Nt-inh1 sense construct (FIG. 7). Total RNA from leaf material was blotted. The blot was hybridised with a Nt-inh1 probe, which was generated by PCR amplification of a Nt-inh1 cDNA clone of full length. Both marked bands correspond to the two transcripts produced in the transgenic plants, whereby transcription either stopped immediately after the end of the cloned Nt-inh1-cDNA or continued to the OCS terminator. The shorter transcript (band of 0,8 kb) corresponds in length to the wild-type transcript. Lines 3 and 4 show a co-suppression effect, which is characterised by a decrease of the amount of endogenous Nt-inh1-transcripts and an increased dry weight/seed and an increased content of stored oil/seed. The increased dry weight of the seeds and increased content of stored oil of the seeds due to co-suppression is shown in Table 4.

TABLE 4

Influence of BinAR-35S-Nt-inh1 sense constructs in transgenic tobacco lines on the dry weight and stored oil content of seeds due to co-suppression effects (see also Northern blot analysis in FIG. 7).

| Line | Dry Weight of Seeds (% in comparison to wild-type) | Oil Content of Seeds (% in comparison to wild-type) |
|---|---|---|
| Wild-type | 100 + 8 | 100 + 12 |
| Cosupp. Nt-inh1-3 | 109 + 7 | 123 + 11 |
| Cosupp. Nt-inh1-4 | 112 + 7 | 132 + 15 |

The Sequence of the Nt-inh1-cDNA antisense strand with base substitution marked is shown in FIG. 8. The base substitutions were obtained by amplification with Taq polymerase. The transformation of tobacco plants with the Nt-inh-antisense construct shown (BinAR-35S-Nt-inh1-antisense$_{mut}$3; cloning strategy is shown in FIG. 6), which has three base substitutions in comparison to the sequence of the wild-type Nt-inh1-sequence, resulted in three independent tobacco lines, which also showed an increased dry weight/seed and an increased content of stored oil/seed (see Table 5). Base substitutions were done at positions 82(g[WT] by c), 135 (a[WT] by g), and 390 (g[WT] by a). Shown is the sequence of the Nt-inh1-sense strand.

TABLE 5

Influence of a BinAR-35S-Nt-inh1 antisense construct with three base substitutions in transgenic tobacco lines on the dry weight and stored oil content of seeds due to antisense-effects upon transformation (see FIG. 8). Shown is data of three transformant lines.

| Line | Dry Weight of Seed (% in comparison to WT) | Content of Stored Oil of Seeds (% in comparison to WT) |
|---|---|---|
| WT | 100 + 8 | 100 + 12 |
| antisense-Nt-inh1mut3-1 | 115 + 7 | 126 + 11 |
| antisense-Nt-inh1mut3-11 | 111 + 7 | 118 + 15 |
| antisense-Nt-inh1mut3-7 | 108 + 6 | 121 + 13 |

The invention claimed is:

1. A process for producing a transgenic plant, whose seeds have an increased amount of reserve material in comparison with a wild-type plant due to the reduction or elimination of the expression of an endogenous invertase inhibitor protein during the development of seeds so that the activity of invertase, which is subject to a regulation by the invertase inhibitor protein, is increased during the development of seeds leading to an increased accumulation of reserve material in the seed, comprising the steps of:
   (a) obtaining a nucleotide sequence expressed during seed development in flowers with young ovules, wherein the nucleotide sequence expressed during said seed development is a nucleotide sequence coding for the endogenous apoplastic invertase inhibitor protein;
   (b) inserting the DNA nucleotide sequence in a DNA construct in sense orientation next to a promoter as a regulatory unit;
   (c) transforming a plant cell of the same plant species from which the nucleotide sequence was obtained, with the DNA construct; and
   (d) cultivating the plant cell and regenerating a plant, wherein the expression of the endogenous invertase inhibitor protein is reduced or eliminated during seed development.

2. The process according to claim 1, wherein the nucleotide sequence coding for the endogenous apoplastic invertase inhibitor protein is a cDNA, obtained by the following steps:
   (a) separating and purifying an inhibitor protein fraction from the cell wall protein fraction of flowers with young ovules of a plant;
   (b) digesting the inhibitor protein and separation of the resulting peptides;
   (c) sequencing the peptides in order to obtain the amino acid sequences;
   (d) deriving nucleotide sequences from the amino acid sequences and designing of primers; and
   (e) cloning a partial or full-length cDNA coding the endogenous apoplastic invertase inhibitor protein from a cDNA library from flowers with young ovules of said plant or alternatively synthesizing the partial or full-length cDNA using the primers.

3. The process according to claim 1, in which the promoter is a constitutive or inducible promoter.

4. The process according to claim 3, in which the promoter is selected from the group consisting of CaMV35S promoter, ubiquitin promoter, and zein promoter from corn.

5. The process according to claim 1, in which the DNA construct has additional regulatory units.

6. The process according to claim 5, in which an additional regulatory unit is a transcription termination signal.

7. The process according to claim 6, in which the transcription termination signal comes from a NOS gene of *Agrobacterium tumefaciens*.

8. The process according to claim 1, in which the plant cell is a cell of a dicotyledonous or monocotyledonous plant.

9. The process according to claim 8, in which the plant cell is from a plant selected from the group consisting of rape, sunflower, peanut, soy bean, oil palm, rice, corn, wheat, barley, oats, rye, pea, *Calendula officinalis, Coriandrum sativum, Crambe abyssinica, Cuphea* ssp., *Dimorphotheca pluvialis, Euphorbia lagascae, Euphorbia lathyris, Lesquerella grandiflora, Limnanthes alba, Linum usitatissimum, Lunaria annua, Lunaria biennis, Oenothera* ssp., *Ricinus communis* and *Simmondsia chinensis*.

10. The process according to claim 1, in which the DNA construct is in a vector.

11. The process according to claim 10, in which the vector is a plasmid or a virus.

12. The process according to claim 1, in which the transformation of the plant cell is carried out by an *Agrobacterium tumefaciens*-mediated transformation or a biolytic process comprising a step selected from the group consisting of electrically induced DNA absorption, chemically induced DNA absorption, electroporation, macroinjection, microinjection and PEG-mediated transformation.

13. A process for producing a transgenic plant, whose seeds have an increased amount of reserve material in comparison with a wild-type plant due to the reduction or elimination of the expression of an endogenous invertase inhibitor protein during the development of seeds so that the activity of invertase, which is subject to a regulation by the invertase inhibitor protein, is increased during the development of seeds leading to an increased accumulation of reserve material in the seed, said process comprising the steps of:
   (a) obtaining a nucleotide sequence expressed during seed development in flowers with young ovules, wherein the nucleotide sequence expressed during said seed development is a nucleotide sequence of a gene for the endogenous apoplastic invertase inhibitor protein;
   (b) inserting the DNA nucleotide sequence in a DNA construct in sense and anti-sense orientation next to a promoter as a regulatory unit, so as to obtain a double-stranded RNA and/or inverted repeat RNA of the endogenous invertase inhibitor gene;
   (c) transforming a plant cell of the same plant species from which the nucleotide sequence was obtained, with the DNA construct, and
   (d) cultivating the plant cell and regenerating a plant, wherein the expression of the endogenous invertase inhibitor protein is reduced or eliminated during seed development.

14. The process according to claim 13, wherein the DNA construct encodes a single-self complementary hairpin RNA of the endogenous invertase inhibitor gene.

15. The process according to claim 13, wherein the DNA construct comprises one copy of the nucleotide sequence of the endogenous invertase inhibitor gene in sense orientation and another copy in anti-sense orientation.

16. The process according to claim 15, wherein the two copies flank a spacer fragment which is non-homologous to the nucleotide sequence used.

17. The process according to claim 13, wherein the nucleotide sequence of the endogenous apoplastic invertase inhibitor protein is a cDNA, obtained by the following steps:
  (a) separating and purifying an inhibitor protein fraction from the cell wall protein fraction of flowers with young ovules of a plant;
  (b) digesting the inhibitor protein and separation of the resulting peptides;
  (c) sequencing the peptides in order to obtain the amino acid sequences;
  (d) deriving nucleotide sequences from the amino acid sequences and designing primers; and
  (e) cloning a partial or full-length cDNA coding the apoplastic invertase inhibitor protein from a cDNA library from flowers with young ovules of said plant or alternatively synthesizing the partial or full-length cDNA using the primers.

18. The process according to claim 13, in which the promoter is a constitutive or inducible promoter.

19. The process according to claim 18, in which the promoter is selected from the group consisting of CaMV35S promoter, ubiquitin promoter, and zein promoter from corn.

20. The process according to claim 13, in which the DNA construct further comprises at least one additional regulatory unit.

21. The process according to claim 20, in which at least one said additional regulatory unit is a transcription termination signal.

22. The process according to claim 21, in which the transcription termination signal comes from the NOS gene of *Agrobacterium tumefaciens*.

23. The process according to claim 13, in which the plant cell is a cell of a dicotyledonous or monocotyledonous plant.

24. The process according to claim 23, in which the plant cell is from a plant selected from the group consisting of rape, sunflower, peanut, soy bean, oil palm, rice, corn, wheat, barley, oats, rye, pea, *Calendula officinalis, Coriandrum sativum, Crambe abyssinica, Cuphea* ssp., *Dimorphotheca pluvialis, Euphorbia lagascae, Euphorbia lathyris, Lesquerella grandiflora, Limnanthes alba, Linum usitatissimum, Lunaria annua, Lunaria biennis, Oenothera* ssp., *Ricinus communis* and *Simmondsia chinensis*.

25. The process according to claim 13, in which the DNA construct is in a vector.

26. The process according to claim 25, in which the vector is a plasmid or a virus.

27. The process according to claim 13, in which the transformation of the plant cell is carried out by means of *Agrobacterium tumefaciens*-mediated transformation or a biolytic process comprising a step selected from the group consisting of electrically induced DNA absorption, chemically induced DNA absorption, electroporation, macroinjection, microinjection and PEG-mediated transformation.

* * * * *